(12) United States Patent
Ishikawa et al.

(10) Patent No.: US 9,005,757 B2
(45) Date of Patent: Apr. 14, 2015

(54) METAL-SALEN COMPLEX COMPOUND AND METHOD FOR PRODUCING THE SAME

(75) Inventors: Yoshihiro Ishikawa, Tokyo (JP); Haruki Eguchi, Tokyo (JP)

(73) Assignees: IHI Corporation, Tokyo (JP); Yoshihiro Ishikawa, Tokyo (JP)

( * ) Notice: Subject to any disclaimer, the term of this patent is extended or adjusted under 35 U.S.C. 154(b) by 0 days.

(21) Appl. No.: 13/996,288

(22) PCT Filed: Dec. 21, 2011

(86) PCT No.: PCT/JP2011/079630
§ 371 (c)(1),
(2), (4) Date: Sep. 24, 2013

(87) PCT Pub. No.: WO2012/086683
PCT Pub. Date: Jun. 28, 2012

(65) Prior Publication Data
US 2014/0011032 A1    Jan. 9, 2014

(30) Foreign Application Priority Data

Dec. 21, 2010  (JP) ................................. 2010-285075
Feb. 25, 2011  (JP) ................................. 2011-040233

(51) Int. Cl.
| | | |
|---|---|---|
| A61K 31/555 | (2006.01) | |
| A61P 35/00 | (2006.01) | |
| C07F 15/02 | (2006.01) | |
| B32B 5/16 | (2006.01) | |
| A61K 31/28 | (2006.01) | |

(52) U.S. Cl.
CPC .................................... A61K 31/28 (2013.01)

(58) Field of Classification Search
USPC .................... 428/402; 424/489, 490; 128/899
IPC ........ C07C 251/24; A61K 31/555; A61P 35/00; C07F 15/02
See application file for complete search history.

(56) References Cited

U.S. PATENT DOCUMENTS

| | | | |
|---|---|---|---|
| 5,549,915 A * | 8/1996 | Volkonsky et al. | 424/490 |
| 5,651,989 A * | 7/1997 | Volkonsky et al. | 424/490 |
| 5,705,195 A * | 1/1998 | Volkonsky et al. | 424/490 |
| 8,268,048 B2 * | 9/2012 | Subramaniam et al. | 95/138 |
| 2007/0134338 A1 * | 6/2007 | Subramaniam et al. | 424/489 |
| 2009/0164484 A1 * | 6/2009 | Horowitz et al. | 707/100 |
| 2009/0169484 A1 | 7/2009 | Eguchi et al. | |
| 2010/0089236 A1 | 4/2010 | Subramaniam et al. | |
| 2012/0029167 A1 * | 2/2012 | Ishikawa et al. | 530/323 |
| 2012/0259155 A1 * | 10/2012 | Ishikawa et al. | 600/12 |
| 2013/0029399 A1 * | 1/2013 | Ishikawa et al. | 435/188 |

FOREIGN PATENT DOCUMENTS

| | | |
|---|---|---|
| CN | 10 2918118 | 2/2013 |
| JP | 2001-010978 | * 1/2001 |
| JP | 2002 500177 | 1/2002 |
| JP | 2004-262810 | 9/2004 |
| JP | 2009-173631 | * 8/2009 |
| JP | 2009 196913 | 9/2009 |
| WO | 94 16683 | 8/1994 |
| WO | 2006 133354 | 12/2006 |
| WO | 2008-001851 | 1/2008 |
| WO | 2010-058280 | 5/2010 |
| WO | 2011-135784 | 11/2011 |
| WO | 2011-151978 | 12/2011 |
| WO | 2012-086683 | 6/2012 |

OTHER PUBLICATIONS

Journal of American Chemical Society, 2005, vol. 127, No. 27, pp. 9698-9699.*
International Search Report, International Application No. PCT/JP2011/079630, Filed Dec. 21, 2011, Mailed Apr. 3, 2012, ISA/Japanese Patent Office.
Journal of American Chemical Society, 2005, vol. 127, No. 27, p. 9698-9699.
Chad A. Johnson et al. "Nanoparticulate Metal Complexes Prepared with Compressed Carbon Dioxide: Correlation of Particle Morphology with Precursor Structure" Journal of American Chemical Society, vol. 127, 27, pp. 9698-9699.

* cited by examiner

*Primary Examiner* — Leszek Kiliman
(74) *Attorney, Agent, or Firm* — Brundidge & Stanger, P.C.

(57) ABSTRACT

The present invention provides a metal-salen complex compound having a controlled grain size that enables the metal-salen complex compound to exert its pharmacological effects as a medicine, at a target region. This metal-salen complex compound is composed of the following that has a crystal grain size of 8 μm or less, and that is represented by the chemical formula below.

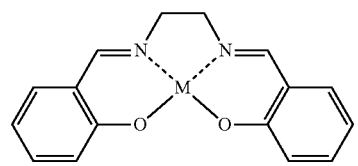

N,N'-Bis(salicylidene)ethylenediamine metal
M is Fe, Cr, Mn, Co, Ni, Mo, Ru, Rh, Pd, W, Re, Os, Ir, Pt, Nd, Sm, Eu, or Gd.

8 Claims, 2 Drawing Sheets

500 nm 500 nm

METAL-SALEN COMPLEX COMPOUND AND METHOD FOR PRODUCING THE SAME

FIELD OF THE INVENTION

The present invention relates to a metal-salen complex compound and a method for producing the metal-salen complex compound. The metal-salen complex compound has magnetic properties, and is used, for example, in magnetic materials and magnetic drugs.

BACKGROUND OF THE INVENTION

Generally, when a drug is administered into a living body, it reaches an affected site and exerts its pharmacological effects at that affected site, thereby exerting its therapeutic effects. On the other hand, it will not be therapeutic if the drug reaches tissues other than the affected site (that is, normal tissues).

Therefore, how to efficiently guide the drug to the affected site is important. A technique to guide the drug to the affected site is called drug delivery, which has been actively studied and developed in recent years. This drug delivery has at least two advantages. One advantage is that a sufficiently high drug concentration may be obtained at the affected tissue. Pharmacological effects will not be seen unless the drug concentration at the affected site is a constant value or more. The therapeutic effects cannot be expected if the concentration is low.

The second advantage is that the drug is guided to only the affected tissue and, therefore, adverse reactions to normal tissues may be inhibited.

Such drug delivery is most effective for cancer treatments by antitumor agents. Most antitumor agents inhibit the cell growth of cancer cells which divide actively, so that the antitumor agents will also inhibit the cell growth of even the normal tissues in which cells divide actively, such as the bone marrow, the hair roots, or the gastrointestinal mucosa.

Therefore, cancer patients to whom the antitumor agents are administered suffer adverse reactions such as anemia, hair loss, and vomiting. Since such adverse reactions impose heavy burdens on the patients, the dosage needs to be limited, thereby causing a problem of incapability to sufficiently obtain the pharmacological effects of the antitumor agents.

Alkylation antineoplastic agent among such antineoplastic agents is a generic term for antitumor agents having the ability to combine an alkyl group ($-CH_2-CH_2-$) with, for example, a nucleic acid protein. DNA is alkylated and DNA replication is inhibited, causing cell death. This action works regardless of cell cycles, also works on cells of the $G_0$ period, has a strong effect on cells which grow actively, and tends to damage, for example, the bone marrow, the gastrointestinal mucosa, the germ cells, or the hair roots.

Moreover, antimetabolite antineoplastic agents are compounds having structures similar to those of nucleic acids or metabolites in a protein synthesis process, impairs cells by, for example, inhibiting synthesis of the nucleic acids, and specifically acts on the cells in mitotic phase.

Furthermore, antitumor antibiotics are chemical substances produced by microorganisms, have actions such as DNA synthesis inhibition and DNA strand breaking, and exhibit antitumor activity.

Also, microtubule inhibitors have antitumor effects by directly acting on microtubules that serve important roles to maintain normal functions of cells, for example, by forming spindles during cell division, placing intracellular organelles, and transporting substances. The microtubule inhibitors act on, for example, cells which divide actively, and nerve cells.

Moreover, platinum preparations inhibit DNA synthesis by forming DNA strands, interchain bonds, or DNA-protein bonds. Cisplatin is a representative drug, but it causes severe nephropathy and requires a large amount of fluid replacement.

Furthermore, parahormone antineoplastic agents are effective against hormone-dependent tumors. Female hormones or antiandrogens are administered to an androgen-dependent prostate cancer.

Also, molecular target drugs are used for treatments targeted at molecules that correspond to molecular biological characteristics specific to each malignant tumor.

Moreover, topoisomerase inhibitors are enzymes for temporarily generating breaks in DNA, and changing the number of tangles of DNA strands. Topoisomerase inhibitor I is an enzyme that generates breaks in one strand of a circular DNA, lets the other strand pass, and then closes the breaks; and topoisomerase inhibitor II is an enzyme that temporarily breaks both the two strands of the circular DNA, lets the other two DNA strands pass between the former two strands, and reconnects the broken strands.

Furthermore, nonspecific immunopotentiators inhibit cancer cell growth by activating the immune system.

An example of a specific method for drug delivery is the use of a carrier. This is to load the carrier, which tends to concentrate on the affected site, with the drug, and have the carrier carry the drug to the affected site.

A promising candidate for the carrier is a magnetic substance, and a method of attaching the carrier which is a magnetic substance, to the drug, and allowing the carrier to be accumulated at the affected site with a magnetic field is proposed (see, for example, Japanese Patent Application Laid-Open Publication No. 2001-10978).

However, when using the magnetic substance carrier as a carrier, it has been found that it is difficult to orally administer the magnetic substance carrier, carrier molecules are generally giant, and there are technical problems in the binding strength and affinity between the carrier and the drug molecules; and it has been difficult to put the magnetic substance carrier to practical use in the first place.

Therefore, the inventors of the present invention suggested a local therapeutic drug in which side chains for giving positive or negative spin charge density are bonded to a basic skeleton of an organic compound, and the local therapeutic drug in its entirety is suitably guided with an external magnetic field by sharing magnetism; and when the local therapeutic drug is applied to a human body or an animal, the local therapeutic drug is retained in the region where a magnetic field is applied locally by a magnetic field outside the body and medicinal effects that the local therapeutic drug originally possess, are exerted on the above region (WO 2008/001851). This therapeutic drug is auto-magnetic and does not rely on magnetic substance carriers. The publication discloses an iron-salen complex compound as one such drug. Japanese Patent Application Laid-Open Publication No. 2009-173631 discloses anti-tumor agents containing iron-salen complex compounds.

Furthermore, the inventors of the present application have proposed various medicines capable of binding, for example, medicinal molecules to a metal salen complex, and guiding them to a target region of an individual with a magnetic field (WO 2010/058280).

PRIOR ART DOCUMENTS

Patent Documents

Patent Document 1: Japanese Patent Application Laid-Open Publication No. 2001-10978
Patent Document 2: WO 2008/001851
Patent Document 3: Japanese Patent Application Laid-Open Publication No. 2009-173631
Patent Document 4: WO 2010/058280

SUMMARY OF THE INVENTION

Problem to be Solved by the Invention

When the grain size of a metal-salen complex is small, a required magnetism cannot be exerted. On the other hand, when the grain size of the metal-salen complex is large, the metal-salen complex cannot pass through capillaries. Thus, the grain size of a metal-salen complex is preferably of a grain size that is applicable to a living body as a medicine without clogging the capillaries, and that may be guided to a target region with a magnetic field.

On the other hand, even if the crystal grain size of the metal-salen complex is of a crystal grain size that leads to difficulty in passing through the capillaries, the usability of the metal-salen complex may be further improved if the dynamics of the metal-salen complex can be controlled, such as by inducing the metal-salen complex to be retained in the affected tissue with a magnetic field after local application to the affected tissue.

The first object of the present invention is to provide a metal-salen complex compound which is controlled to have an appropriate crystal grain size. In addition, the second object of the present invention is to provide a metal-salen complex compound that can be locally applied to a target region such as an affected tissue. Furthermore, the third object of the present invention is to provide a metal-salen complex compound having a grain size capable of being guided to the target region with a magnetic field even when the metal-salen complex compound is systemically applied to a living body as a medicine. Further still, the fourth object of the present invention is to provide a method for producing these metal-salen complex compounds.

Means for Solving the Problem

To achieve the above objects, the crystal grain size of the metal-salen complex compound according to the present invention is confined to a crystal grain size that will not clog the capillaries of humans or animals, and the metal-salen complex compound according to the present invention is characterized by the ability to control the dynamics with an external magnetic field. Considering that the diameter of capillaries are 8 µm to 20 µm, and the grain size of erythrocytes that pass through the capillaries is approximately 8 µm, and the grain size of leukocytes that pass through the capillaries is approximately 8 to 20 µm, the crystal grain size of the metal-salen complex compound of the present invention is desirably 8 µm or less; preferably 1 µm or more to 8 µm or less; more preferably 1 µm or more to 5 µm or less, and even more preferably 1 µm or more to 3 µm or less. The metal-salen complex compound is auto-magnetic, and is capable of being retained in the affected site with an external magnetic field after, for example, local application to an affected site.

When the grain size of the metal-salen complex compound is less than 1 µm, the magnetism which allows the metal-salen complex compound to be retained locally with an external magnetic field declines, and it is possible that the metal-salen complex compound may leak into capillaries outside the target affected tissue, from the target affected tissue. Thus, when the metal-salen complex compound is locally applied to the affected site, the minimum crystal grain size of the metal-salen complex compound is desirably 1 µm. The percentage of metal-salen complex compounds with a crystal grain size of 1 µm or more to 3 µm or less, is preferably 70% or more.

For the metal-salen complex compound to reach the affected site by systemic application, and for the metal-salen complex compound to be retained in the affected site with a magnetic field, the crystal size of the metal-salen complex is of 1 µm or less so that the metal-salen complex compounds may pass through a large number of capillaries, and the percentage of the metal-salen complex compounds with a crystal grain size of 100 nm or more to 500 nm or less is preferably 70% or more.

When the grain size of the metal-salen complex compound exceeds 1 µm, it is possible that the metal-salen complex compound may not be able to pass through the capillaries. When the grain size of the metal-salen complex compound is less than 100 nm, the ferromagnetism required for magnetic guidance cannot be obtained sufficiently. On the other hand, when the grain size exceeds 500 nm, the metal-salen complex compound may not pass through the capillaries with ease. When the percentage of particles with a grain size of 100 nm or more to 500 nm or less, is less than 70%, the proportion of the grains where the properties for passing through the capillaries is insufficient increases. The grain size is preferably 200 nm or more to 400 nm or less, the grain size is even more preferably 250 nm or more to 350 nm or less.

The metal-salen complex compound of the present invention generally refers to metal complexes with salen as the ligand, and also includes derivative substitutions and derivatives of metal complexes. The structural formula of the metal-salen complex compound is as indicated below in Formula (I). Each of "a" to "h" may represent hydrogen, or at least one of "a" to "h" may be substituted with functional groups/substituents other than hydrogen.

Derivatives of the metal-salen complex compound of the present invention includes metal-salen complex compounds or their derivative substitutions bound to functional molecules such as medicinal molecules, enzymes, and antibodies, as in, for example, WO 2010/058280. The disclosure made in the publication is incorporated in the specification of the present application by reference in its entirety. The derivative of the metal-salen complex compound in complex with a medicinal molecule is useful as a carrier for guiding or localizing the medicinal molecules at the target affected tissue.

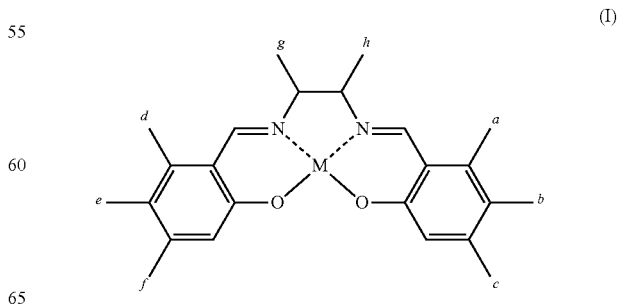

(I)

N,N'-Bis(salicylidene)ethylenediamine metal

In Formula (I), "M" represents Fe, Cr, Mn, Co, Ni, Mo, Ru, Rh, Pd, W, Re, Os, Ir, Pt, Nd, Sm, Eu, or Gd.

Preferred embodiments of locally applying the metal-salen complex compound of the present invention to the affected tissue of a human body or an animal involves an arterial injection into an artery in the vicinity of the affected tissue, or an injection into the affected tissue itself. Publicly known embodiments such as ointments, lotions, or adhesive skin patches may be adopted as other embodiments of local application. Embodiments of systemically applying the metal-salen complex compound involve an intravenous injection and/or an infusion injection. Typical prescription examples of injections and infusions of the metal-salen complex compound involve physiological saline as a solvent, and suspensions or opalizers may be used. The metal-salen complex compound of the present invention is preferably used as an anti-tumor agent, as disclosed in the above prior art. Other uses include use as a carrier for drug delivery of the medicinal molecule by binding the metal-salen complex compound to another medicinal molecule as mentioned above, and furthermore, use as an MRI diagnostic agent.

When applying the metal-salen complex compound of the present invention to an individual (a human or an animal), by providing a magnetic field (500 mT to 1 T (1,000 mT)) to a target region where the affected organ or the affected tissue is present, the metal-salen complex compound may be guided to or retained at the target affected region at least while magnetism is provided.

Effects of the Invention

As described above, according to the present invention, a metal-salen complex compound which is controlled to have an appropriate crystal grain size may be provided. Furthermore, according to the present invention, a metal-salen complex compound that can be locally applied to a target region such as an affected tissue may be provided. Further still, the present invention can provide a metal-salen complex compound having a grain size capable of being guided to the target region with a magnetic field even when the metal-salen complex compound is systemically applied to a living body as a medicine. Furthermore, the present invention can provide a method for producing these metal-salen complex compounds.

DESCRIPTION OF EMBODIMENTS

Example I

Figure 1:
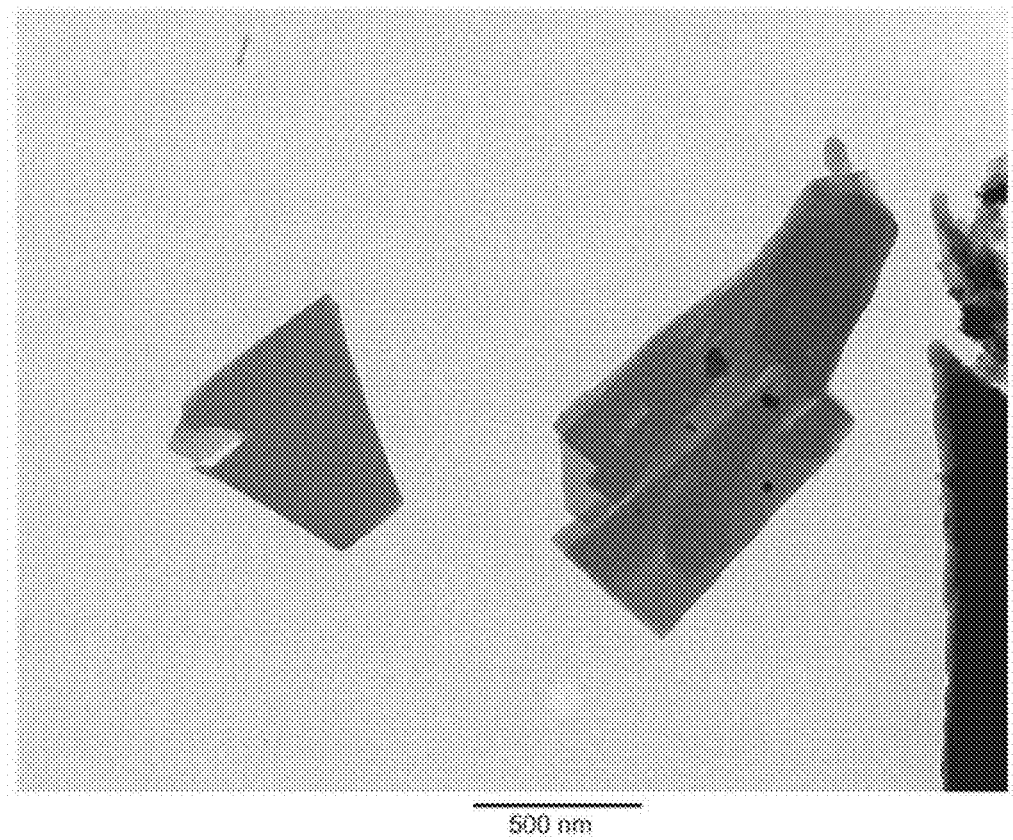
FIG. 1 is a photograph taken with a transmission electron microscope, of iron-salen complex compounds in which the crystal grain size is coarse (the long side exceeding 1 μm), according to an example (Example I) of the present invention.

Local Application of Metal-Salen Complex Compounds (Iron-Salen Complex Compounds)

Example I-1

Production of Metal-Salen Complex Compounds

A salen ligand (N,N'-Bis(salicylidene)ethylenediamine) and its derivatives are synthesized by a dehydration condensation reaction of derivatives of salicylaldehyde and ethylenediamine that correspond to a salen ligand (N,N'-Bis(salicylidene)ethylenediamine) and its derivatives. After the resulting ligand becomes a derivative of phenoxide ion, or by causing the obtained ligand to react with a metal ion under basic conditions, a metal-salen complex is obtained. Details are described hereinafter.

Step 1:

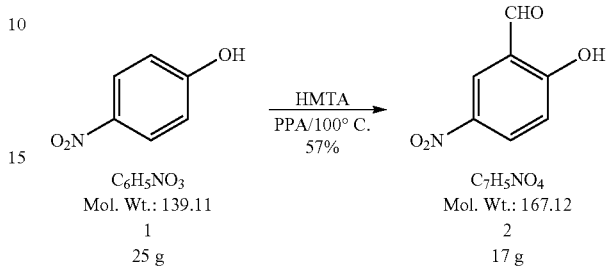

$C_6H_5NO_3$
Mol. Wt.: 139.11
1
25 g $C_7H_5NO_4$
Mol. Wt.: 167.12
2
17 g

A mixture of 4-nitrophenol (25 g, 0.18 mol), hexamethylene tetramine (25 g, 0.18 mol), and polyphosphoric acid (200 ml) was stirred for 1 hour at 100° C. Thereafter, the mixture was introduced into 500 ml of ethyl acetate and 1 L of water, and was stirred until complete dissolution. Upon further adding 400 ml of ethyl acetate to the solution, the solution separated into two phases, the aqueous phase was removed, and the remaining compounds were washed twice with a basic solvent and dried with anhydrous $Mg_2SO_4$, allowing 17 g of Compound 2 to be synthesized (57% yield).

Step 2:

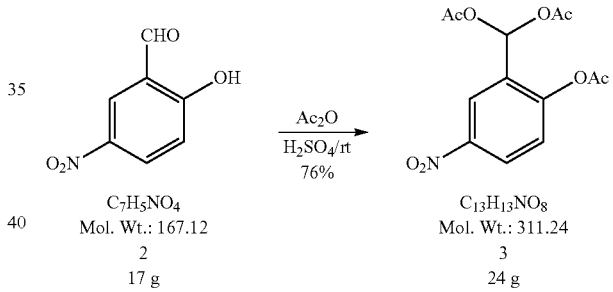

$C_7H_5NO_4$
Mol. Wt.: 167.12
2
17 g $C_{13}H_{13}NO_8$
Mol. Wt.: 311.24
3
24 g

Compound 2 (17 g, 0.10 mol), acetic anhydride (200 ml), and $H_2SO_4$ (in small quantities) were stirred for 1 hour at room temperature. The resulting solution was mixed for 0.5 hour in ice water (2 L) to bring about hydrolysis. Upon filtering and drying the resulting solution in the atmosphere, white powder was obtained. Upon recrystallizing the powder using a solution containing ethyl acetate, 24 g of Compound 3 (76% yield) in the form of white crystals was obtained.

Step 3:

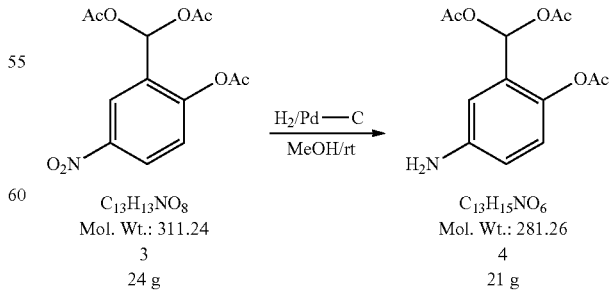

$C_{13}H_{13}NO_8$
Mol. Wt.: 311.24
3
24 g $C_{13}H_{15}NO_6$
Mol. Wt.: 281.26
4
21 g

A mixture of Compound 3 (24 g, 77 mmol), methanol (500 ml), and carbon (2.4 g) carrying 10% palladium was reduced overnight in a 1.5 atm hydrogen reducing atmosphere. After reduction has been completed, the product was filtered, allowing Compound 4 (21 g) in the form of brown oil to be synthesized.

Steps 4 and 5:

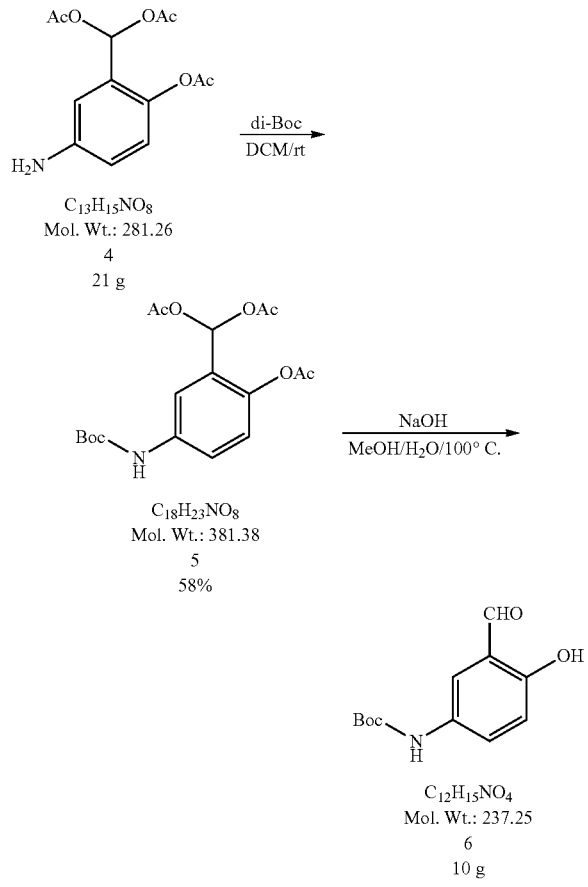

Compound 4 (21 g, 75 mmol) and di(tert-butyl)dicarbonate (18 g, 82 mmol) were stirred overnight in anhydrous dichloromethane (DCM) (200 ml) in a nitrogen atmosphere. After allowing the resulting solution to evaporate in a vacuum, the resulting solution was dissolved in methanol (100 ml). Sodium hydroxide (15 g, 374 mmol) and water (50 ml) were then added, and the solution was brought to reflux for 5 hours. The solution was then cooled, filtered, washed with water, and allowed to dry in a vacuum, thereby giving a brown compound. The resulting compound was processed twice by flash chromatography using silica gel, thereby giving 10 g of Compound 6 (58% yield).

Step 6:

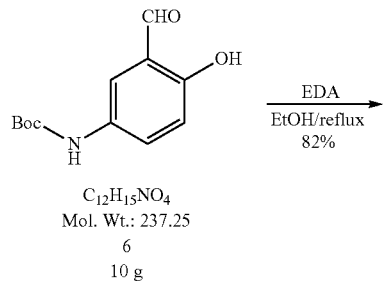

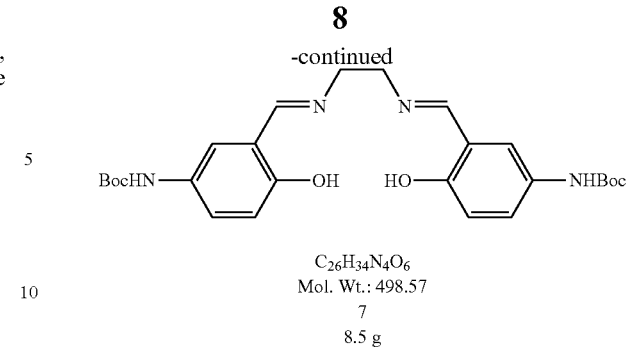

Compound 6 (10 g, 42 mmol) was introduced into 400 ml of anhydrous ethanol, was brought to reflux while heated, and several drops of ethylenediamine (1.3 g, 21 mmol) were added to 20 ml of anhydrous ethanol while stirring for 0.5 hour. Next, the mixed solution was introduced into a container containing ice, where the mixed solution was cooled and stirred for 15 minutes. The mixed solution was then washed with 200 ml of ethanol, filtered, and dried in a vacuum, allowing 8.5 g of Compound 7 (salen) to be synthesized (82% yield).

Step 7:

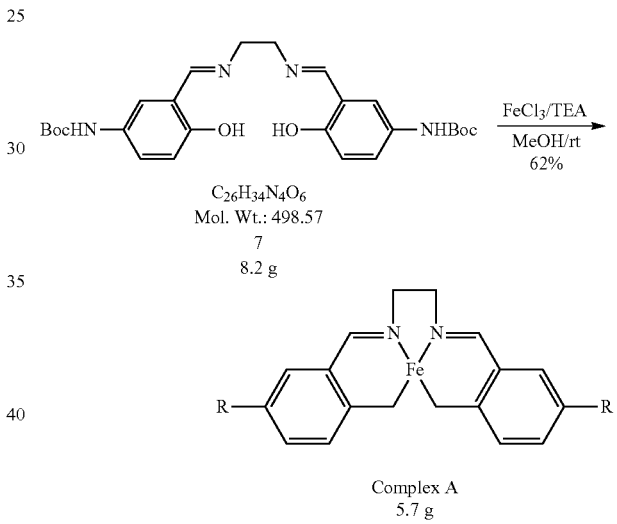

Compound 7 (8.2 g, 16 mmol) and triethylamine (22 ml, 160 mmol) were introduced into anhydrous methanol (50 ml), and a solution where $FeCl_3$ (2.7 g, 16 mmol) has been added to 10 ml of methanol, were mixed under a nitrogen atmosphere. Upon mixing the solution in a nitrogen atmosphere for 1 hour at room temperature, a brown compound was obtained. The resulting compound was heated to 80° C., and was then slowly cooled (for example, 10 hours to 12 hours) by, for example, air cooling to room temperature. The solution was filtered, and the crystal residue was allowed to dry in a vacuum. The resulting crystal was washed with 400 ml of dichloromethane twice, and with a basic solution (tetrahydrofuran) twice, and was dried with $Na_2SO_4$, and was allowed to further dry in a vacuum, thereby giving Complex A (an iron-salen complex compound (where all of "a" to "h" represent H). This compound was recrystallized in a solution of diethyl ether and paraffin, and measurements of the crystal by high-performance liquid chromatography revealed 5.7 g of Complex A (62% yield) with a purity of 95% or more. Recrystallization is carried out under similar slow cooling conditions as described above. The reaction in Step 7 may also be carried out under heating. Heating of the resulting compound is not required in this case.

When a metal complex other than an iron-salen complex compound is used, metal chlorides other than iron, such as $MCl_3$, may be used in place of $FeCl_3$. The fact that a Mn-salen complex, a Cr-salen complex, and a Co-salen complex which are not iron-salen complex compounds, possess magnetic properties that allow the Mn-salen complex, the Cr-salen complex, and the Co-salen complex to be guided with an external magnetic field, is as disclosed in Japanese Patent Application No. 2009-177112 filed by the same applicants as those of the present application. In addition, it is apparent from Japanese Patent Application Laid-Open Publication No. 2009-173631 that metals such as an iron-salen complex compound have anti-tumor effects. The disclosure made in these prior applications is incorporated in the present application by reference in its entirety.

Example I-2

Measurement of Grain Size

Next, the grain size of the crystal grain after recrystallization is measured. First, approximately 2 g of crystals are weighed, and the crystals are ground in a mortar for approximately 30 minutes. The ground crystals are collected, weighed again, the dilute amount of the solvent (physiological saline) is determined, and the crystals are diluted with the solvent with the foregoing dilute amount. The concentration of crystal grains at this time is 20 mM.

Thereafter, 50 ml of the solution is then poured into a tube, 20 ml of a solvent is then poured into the tube, and is pulverized by ultrasonic treatment. This treatment is applied while stirring until the grains can longer be seen with the naked eye. Next, the solution is diluted to the precise dilute amount (the actual concentration to be injected intravenously: 9.25 mM), and is filtered using a 40-μm cell strainer (BD Falcon).

The grain size of crystal grains obtained as a result of filtration was measured using electron microscope images. The apparatus used, and for example, the conditions are as follows.

Apparatus: Transmission electron microscope (manufactured by Hitachi, H-7100FA)
Conditions: Accelerating voltage of 100 kV
Sample preparation: Dispersion method (after grinding the crystals in a mortar, pure water was added, and dispersed on the grid by TEM)
Grain size distribution measurement software: Image-Pro Plus (Media Cybernetics, Md., U.S.A.)
Target for measurement: Traced images of the molecules of the iron-salen complex compound in TEM photographs Crystallization and recrystallization were carried out by air cooling, and measurement of the grain size was made (number of samples: 140). The resulting average grain size was 450 nm, while the standard deviation was 360. FIG. 1 is a photograph of representative samples taken with an electron microscope. From this, the presence of crystals with a grain size exceeding 1 μm can be observed, and the percentage of particles with a grain size of 1 μm or more to 3 μm or less is 70% or more (proportion of the incidence of the number of particles) can be observed. The crystals were needle-like in form.

Example I-3

Verification of Magnetism

Ferromagnetism in crystals of a grain size obtained in Example I-1 was verified. Measurement of the magnetic field-magnetization curve using Quantum Design MPMS7, gave hysteresis loops characteristic of ferromagnetic substances at −268° C. to 37° C., revealing that the crystals of a grain size obtained in Example I-1 are ferromagnetic substances.

Next, a melanoma cell (clone M3) was cultured in a round Petri dish, and iron salens were sprinkled evenly. A button magnet with a magnetic flux density of 240 mT was then placed under the Petri dish for 24 hours. As a result, killing of melanoma cells was observed along the edges of the button magnet.

Example I-4

Local Application to Affected Tissue

Rabbit-derived squamous cell carcinomas (VX2) were transplanted into the femoral region of a rabbit, and engraftment was reached 2 to 3 weeks thereafter. Next, the iron-salen complex compounds that have been observed using a transmission electron microscope, in which the grain size was coarse, with a grain size of 1,500 nm (1.5 μm), were diluted to a concentration of 100 μm with physiological saline, and a volume of 5 mg/kg was injected arterially using a catheter. Arterial injection into an artery in the femoral region was performed. This procedure conforms to the procedure detailed in Japan Radiological Society 50(4), 426-428, 1990. Seven days following the initiation of administration of the above volume, it has been observed that, while the tumor volume of a group in which the iron-salen complex compounds had not been injected arterially, revealed to be approximately twice as large as the initial tumor volume, the tumor volume of a group in which the iron-salen complex compounds had been injected arterially, was reduced to 20% of the tumor volume before treatment. When arterial injection is performed, the iron-salen complexes were retained in the affected site by a permanent magnet with a magnetic flux density of 600 mT so that the drug does not leak into other organs. Cell slices of the affect site revealed that the iron-salen complexes were retained in cancer tissues. Prussian blue (ferric hexacyanoferrate and hydrochloric acid) manufactured by Sigma was used for staining.

Example II

Systemic Application of Metal-Salen Complex Compounds (Iron-Salen Complex Compounds)

Example II-1

Production of Metal-Salen Complex Compounds

While cooling was performed by slowly cooling "(for example, 10 hours to 12 hours) by, for example, air cooling to room temperature" in Step 7 of Example I-1, cooling is performed by rapid cooling (cooling rate: 10-30° C./min) by, for example, water cooling with water of room temperature or ice water in the present example. All other procedures are the same as the procedures in Example I.

Example II-2

Measurement of Grain Size

Figure 2:
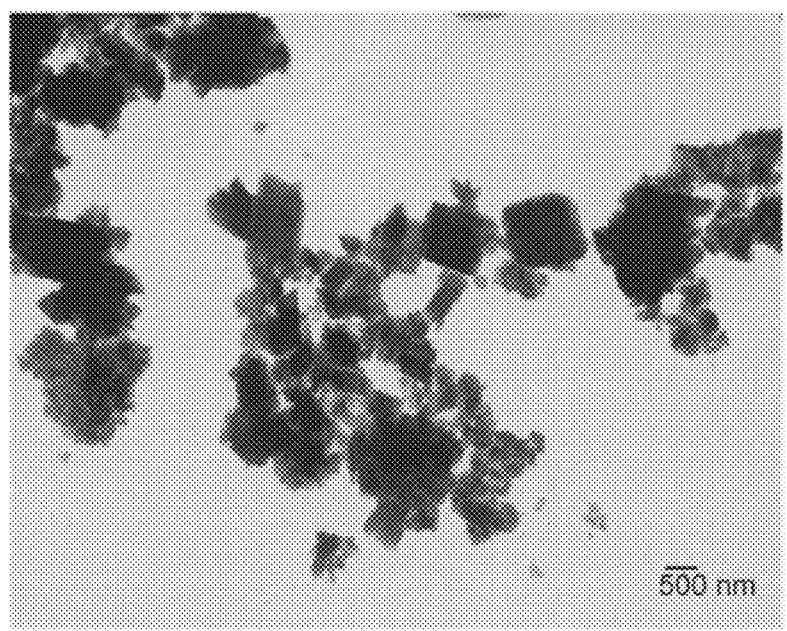
FIG. 2 is a photograph taken with an electron microscope of crystals of iron-salen complex compounds according to an example (Example II) of the present invention.
Figure 3:
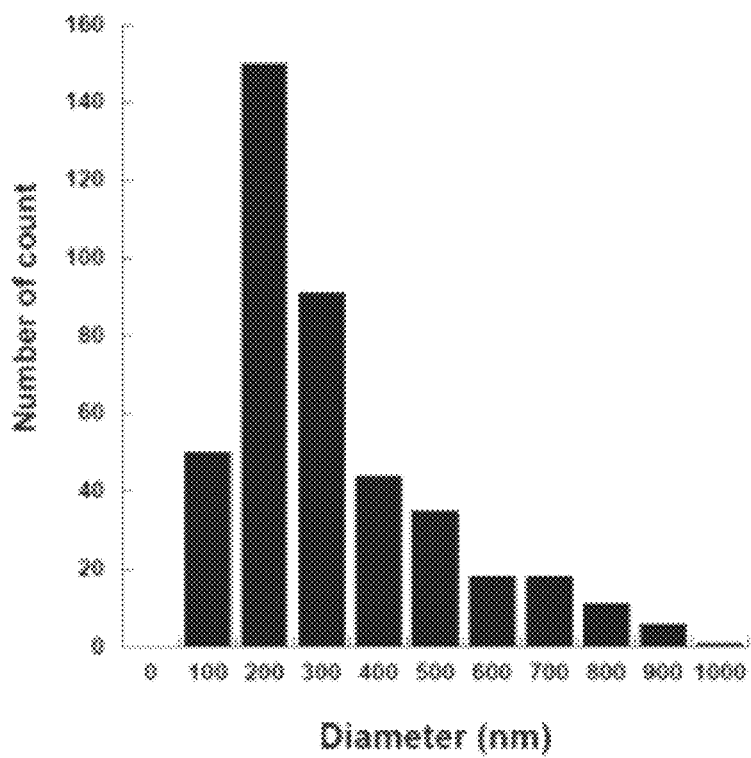
FIG. 3 is a chart showing grain size distribution of crystals of iron-salen complex compounds according to an example (Example II) of the present invention.

The number of samples to be measured is 436. All other procedures for measurement are the same as the procedures in Example I-2. The crystal grain size of each sample was measured twice. The resulting average grain size was 300 nm, while the standard deviation was 300. FIG. 2 is a photograph of representative samples taken with an electron microscope. FIG. 3 shows grain size distribution. From FIG. 3, the percentage of particles with a grain size of 1 μm or less, and a grain size of 100 nm or more to 500 nm or less is 70% or more can be observed. The crystals were needle-like in form.

Example II-3

Verification of Magnetism

Ferromagnetism in crystals of a grain size obtained in Example II-1 was verified by the same method as the method in Example 1-2. The effects on melanoma cells are the same as the effects found in Example I-2.

Example II-4

Capillary Passage

Iron-salen complexes obtained in Example II-1 does not clog capillaries. Even administration into the tail vein of a mouse, of a solution with a concentration of 9.25 mM in which iron salens are dissolved in physiological saline, does not bring about clogging of the blood vessels. Administration into the tail vein of a mouse, of a solution containing iron-salen complex compounds having a crystal grain size of 10 μm (dissolved in physiological saline, concentration of 9.25 mM), clearly brought about clogging of the blood vessels in the lung five seconds later.

Comparative Example I

Verification of Magnetism

Measurement of the magnetic field-magnetization curve using Quantum Design MPMS7, gave hysteresis loops characteristic of superparamagnetic substances at −268° C. to 37° C., revealing that the iron-salen complexes with a grain size of approximately 50 nm are superparamagnetic substances.

While preferred embodiments have been described in the foregoing specification, the same results can be obtained with metal-salen complex compounds other than iron. In addition, "crystal grain size" is the diameter of crystals, and may also be a value obtained mathematically or statistically such as by calculating the average value or the standard deviation of each grain size of the plurality of particles of the metal-salen complex compounds. In the present invention, magnetic medicine refers to the metal-salen complex compound itself, the derivative substitutions of the metal-salen complex, or its derivatives as described above. The magnetic medicine contains salen complex compounds that are active ingredients, at a concentration sufficient to exert pharmacological effects such as antitumor effects.

The invention claimed is:
1. A magnetic medicine comprising:
a metal-salen complex compound for application to an affected tissue of a living body,
wherein the metal-salen complex compound is retained in the affected tissue with an external magnetic field after the application of the metal-salen complex compound to the affected tissue,
wherein the metal-salen complex compound has a crystal grain size of 8 μm or less, and
wherein a percentage of the metal-salen complex compound having a crystal grain size of 1 μm or less, and a crystal grain size of 100 nm or more to 500 nm or less, is 70% or more.
2. The magnetic medicine according to claim 1, wherein the crystal grain size is at least 1 μm.
3. The magnetic medicine according to claim 1, wherein the metal-salen complex compound comprises a compound of Structural Formula (I) below:

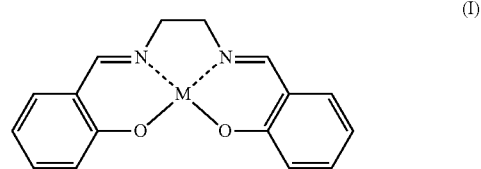

N,N'-Bis(salicylidene)ethylenediamine metal
M is Fe, Cr, Mn, Co, Ni, Mo, Ru, Rh, Pd, W, Re, Os, Ir, Pt, Nd, Sm, Eu, or Gd.
4. The magnetic medicine according to claim 1, wherein the metal-salen complex compound is locally applied to the affected tissue of the living body.
5. The magnetic medicine according to claim 1, wherein the metal-salen complex compound is guided to the affected tissue of the living body with an external magnetic field after the application of the metal-salen complex compound to the affected tissue, the application to the affected tissue being a systemic application.
6. The magnetic medicine according to claim 1, wherein the metal-salen complex compound is an antitumor agent.
7. A method for producing a magnetic medicine comprising:
crystallizing a metal-salen complex compound under a rapid cooling condition.
8. The method for producing the magnetic medicine according to claim 7, further comprising:
allowing salen to react with a metal compound, and then obtaining a crystal particle of the metal-salen complex compound by rapidly cooling a heated reactant.

* * * * *